United States Patent [19]

Shima et al.

[11] Patent Number: 4,988,652

[45] Date of Patent: Jan. 29, 1991

[54] PROCESS FOR RECOVERING CATALYST FOR USE IN PREPARING α-(4-ISOBUTYLPHENYL)PROPIONIC ACID

[75] Inventors: Yoshikazu Shima; Kazuo Tanaka; Yoshifumi Sato, all of Niigata, Japan

[73] Assignee: Mitsubishi Gas Chemical Co., Inc., Tokyo, Japan

[21] Appl. No.: 456,313

[22] Filed: Dec. 26, 1989

[30] Foreign Application Priority Data

Mar. 16, 1989 [JP] Japan ................................. 1-62154

[51] Int. Cl.$^5$ ..................... B01J 38/68; B01J 31/40; C01G 53/02; C07C 51/12
[52] U.S. Cl. ................................. 502/24; 423/140; 423/149; 502/20; 502/31; 502/34; 562/406
[58] Field of Search ................. 502/24, 22, 31, 20, 502/34; 423/140, 149; 562/406

[56] References Cited

U.S. PATENT DOCUMENTS 4,356,320 10/1982 Naglieri et al. .................. 562/406
4,843,172 6/1989 Tanaka et al. .................... 562/406

FOREIGN PATENT DOCUMENTS 2199030 6/1988 United Kingdom .

Primary Examiner—Paul E. Konopka
Attorney, Agent, or Firm—Frishauf, Holtz, Goodman & Woodward

[57] ABSTRACT

An efficient process for recovering a catalyst used in the preparation of α-(4-isobutylphenyl)propionic acid, which comprises recovering part of a nickel catalyst component, such as nickel carbonyl, from a purge gas, concentrating a reaction product mixture, adding an organic solvent thereto to extract the reaction product, then separating and recovering the majority of the catalyst components from the extraction residue.

22 Claims, No Drawings

PROCESS FOR RECOVERING CATALYST FOR USE IN PREPARING α-(4-ISOBUTYLPHENYL)PROPIONIC ACID

BACKGROUND OF THE INVENTION

1. Field of the Invention

This invention relates to a process for effectively recovering catalysts which were used in the industrial preparation of α-(4-isobutylphenyl)propionic acid.

α-(4-Isobutylphenyl)propionic acid is a medical raw material for anti-inflammatory, analgesic and antipyretic drugs.

2. Description of the Related Arts

The present inventors have already proposed a process for producing α-(4-isobutylphenyl)propionic acid by reacting α-(4-isobutylphenyl)ethyl alcohol with carbon monoxide in the presence of a catalyst comprising a nickel compound, a phosphine compound and an iodine compound, preferably further in the presence of a ketone solvent.

In order to make the above process more economical, an additional process in which the used catalyst can be recovered and reused effectively is required to be established.

In a conventional process for recovering a catalyst used in a homogeneous reaction system, reaction products are distilled out and the catalyst is recovered as a residue.

When the above conventional recovering process is applied to the reaction mixture obtained from the said production process for α-(4-isobutylphenyl)propionic acid, the activity of the recovered catalyst was found to be markedly lowered. This is caused by the fact that the activity of the catalyst becomes deteriorated with exposure to the high temperatures because of high boiling point of the product. When the distillation is carried out at a relatively low temperature under a reduced pressure, the by-products having high boiling points are found to be accumulated on the catalyst, so that the activity of the recovered catalyst is gradually lowered.

SUMMARY OF THE INVENTION

An object of the present invention is to provide a process for recovering a catalyst which has been used in a process for producing α-(4-isobutylphenyl)propionic acid with high efficiency.

Another object of the present invention is to provide a process for producing α-(4-isobutylphenyl)propionic acid economically by using the recovered catalyst.

The present invention relates to a process for recovering a catalyst comprising a nickel compound, a phosphine compound and an iodine compound used in the preparation of α-(4-isobutylphenyl)propionic acid by reacting α-(4-isobutylphenyl)ethyl alcohol with carbon monoxide, which process comprises recovering a part of the nickel component as nickel carbonyl from a purge gas, adding an organic solvent to a concentrate of the reaction product mixture to extract the reaction products, and separating and recovering the majority of the catalyst components from the extraction residue.

DESCRIPTION OF THE PREFERRED EMBODIMENTS

A process for producing α-(4-isobutylphenyl)propionic acid is explained.

In a preferred example of the process, α-(4-isobutylphenyl)propionic acid is prepared by reacting α-(4-isobutylphenyl)ethyl alcohol with carbon monoxide in the presence of a catalyst comprising a nickel compound as a main component, a phosphine compound as a catalyst coordinate and an iodine compound as a co-catalyst or an auxiliary catalyst.

A nickel compound such as nickel iodide, nickel acetate, nickel carbonyl complex and the like can be used as the main catalyst component. The preferred amount of the nickel compound to be used is $10^{-3}$ to 1 gram nickel atom per mole of α-(4-isobutylphenyl)ethyl alcohol.

A phosphine compound such as triphenylphosphine, tributylphosphine and the like can be used as the catalyst coordinate. The preferred amount of the phosphine compound to be used is 1 to 6 in terms of the atomic ratio of phosphine to nickel.

As a co-catalyst, an iodine compound such as iodine, methyl iodide and the like can be used. The preferred amount of the iodine compound to be used is 1 to 20 in terms of the atomic ratio of iodine to nickel.

It is also appropriate to use a solvent for the above reaction. Preferable solvents include an aromatic ketone such as acetophenone, and an acyclic ketone such as cyclohexanone.

The preferred amount of the solvents is 1 to 20 parts by weight based on 1 part by weight of α-(4-isobutylphenyl)ethyl alcohol.

The reaction temperature is 50° to 300° C., with the range of 150° to 250° C. being preferred for practical use.

The reaction pressure is 5 to 500 kg/cm$^2$, preferably 10 to 200 kg/cm$^2$ as a carbon monoxide partial pressure.

When the reaction is carried out under the above conditions, α-(4-isobutylphenyl)propionic acid can be produced with a high yield and a high selectivity.

In the following, the process for recovering the catalyst in the present invention is explained in detail.

First, in the preparation of the above α-(4-isobutylphenyl)propionic acid, a part of the nickel component in the charged catalyst as a nickel carbonyl accompanies a purge gas or a dissolved gas generated from the product mixture when discharging the mixture out of the reaction system. This nickel component is collected by a cold trap and recovered (hereinafter called as Recovered Catalyst A).

In Recovered Catalyst A, 10 to 25% of the nickel component in the charged catalyst can be recovered as nickel carbonyl under the usual conditions.

Next, the reaction product mixture drawn out of the reaction system is concentrated, and an organic compound as an extracting solvent is added to the resulting concentrate to extract the reaction product. Then, the majority of the catalyst components can be separated and recovered as a precipitate (hereinafter called as Recovered Catalyst B.)

Recovered Catalyst B can be obtained by the following procedures.

First, the concentration of the reaction product mixture is performed after drawing the mixture out of the reaction system. This concentration can be carried out by evaporation with heating under atmospheric pressure or reduced pressure. It is preferred to reduce the concentration temperature as low as possible in order not to deteriorate the activity of the catalyst recovered. The allowable conditions of the concentration are preferably in the pressure range of atmospheric pressure to 0.1 mmHg and a heating temperature range of 50° to 100° C.

The concentration ratio of the product mixture is in the range of 0 to 100%, preferably 70 to 90% in terms of a removal ratio of the reaction solvent used.

The catalyst recovery process of the present invention can be carried out without the above concentration of the product mixture. But when the concentration is effected, the precipitating efficiency of the catalyst components can be enhanced in the subsequent procedures of extracting the reaction product and precipitating the catalyst.

Next, the product and the catalyst components are separated from the above concentrate to recover the catalyst components.

Preferable examples of the solvents for extracting the product include hydrocarbons such as hexane, heptane, cyclohexane, benzene, and toluene; ethers such as diethyl ether, dioxane, and tetrahydrofuran; and esters such as methyl acetate, and ethyl acetate. Hydrocarbons such as hexane and heptane are particularly preferred.

The amount of these extracting solvents is less than 10 parts, preferably 1 to 5 parts based on 1 part of the concentrate.

The temperature of the extraction is in the range of 0° C. to 120° C., preferably 10° C. to 70° C.

When the procedures are carried out under the above conditions, the reaction product is all extracted in the solvent phase, and simultaneously, almost all of the catalyst components are separated and recovered as precipitates (Recovered Catalyst B).

In Recovered Catalyst B, 70 to 85% of the nickel component is recovered based on the charged catalyst and nearly 100% of the phosphine component and the iodine component are recovered.

When the Recovered Catalyst A and Recovered Catalyst B according to the present invention are mixed to be used again for the reaction, α-(4-isobutylphenyl)-propionic acid can be prepared with sufficient catalytic activity.

The process of the present invention can be performed in either a batch system or a continuous system.

According to the invention, catalyst components in the production of α-(4-isobutylphenyl)propionic acid, can be recovered and reused in simple operations. Thus, an industrial process of preparing α-(4-isobutylphenyl)-propionic acid can be established by the present invention. Accordingly, it has great industrial value.

The process of the present invention is explained in more detail by referring to Examples and Comparative examples, but the present invention is not limited by these Examples.

EXAMPLE 1

In an autoclave made of Hastelloy C having an inner volume of 500 ml were charged 80.0 g of α-(4-isobutylpheyl) ethyl alcohol, 9.4 g of nickel iodide, 11.8 g of triphenylphosphine, 6.4 g of methyl iodide and 200 g of acetophenone as a solvent. Then, carbon monoxide was introduced to the resulting mixture under pressure so that the carbon monoxide partial pressure reached 150 kg/cm$^2$, and reacted at 170° C. for 2 hours.

After completion of the reaction, the autoclave was cooled, the residual gas was purged through a cold trap, and then 317.4 g of the reaction product mixture were obtained. In the cold trap, nickel carbonyl was collected in an amount corresponding to 20.5% of the nickel component in the charged catalyst (Recovered Catalyst A).

The reaction product mixture was analyzed by gas chromatography. The conversion of α-(4-isobutylphenyl)ethyl alcohol was 99.0% and the selectivity to α-(4-isobutyl-phenyl)propionic acid was 85.9%.

About 80% of acetophenone used as a solvent was removed from this reaction product mixture by using an evaporator.

Next, 450.0 g of n-hexane was added thereto and α-(4-isobutylphenyl)propionic acid and by-products were extracted.

Catalyst components precipitated by the above operation were filtered and 24.3 g of the catalyst was recovered (Recovered Catalyst B).

As the results of analysis of Recovered Catalyst B, it was found that the recovery ratios of nickel, phosphorus and iodine based on the charged catalysts were 72%, 99.9% and 99.9%, respectively.

α-(4-Isobutylphenyl)propionic acid was separated and purified by distillation of the hexane extract solution. Nickel in an amount corresponding to 8% of the nickel component in the charged catalysts was contained in the distillation residue.

Recovered Catalyst A and Recovered Catalyst B obtained by the above procedures were mixed with the distillation residue, and the resulting mixture was used again as a catalyst for the preparation of α-(4-isobutylphenyl)propionic acid under the same conditions as described above. As a result, the same catalytic activity as the first reaction could be attained, and the conversion of α-(4-isobutylphenyl)ethyl alcohol was 99.2% and selectivity to α-(4-isobutylphenyl)propionic acid was 86.0%.

In the above procedure, the distillation residue was added to the recovered catalyst as described above. However, the residue can be disposed without resulting in any economical problems because of the small amount of the residue. In the actual process, the distillation residue can be treated as wastes in order to prevent the accumulation of high boiling point materials, and the reaction can be carried out by supplying a corresponding amount of fresh nickel compound instead of using the residue.

COMPARATIVE EXAMPLE 1

After preparing α-(4-isobutylphenyl)propinic acid in the same manner as in Example 1, the catalyst components were recovered by direct distillation of the reaction product mixture under reduced pressure.

This distillation was carried out under the conditions of a reduced pressure of 0.55 mmHg and a temperature of 130° C. to 135° C., which is the boiling point of α-(4-isobutylphenyl)propionic acid.

Using the distillation residue as a catalyst, α-(4-isobutylphenyl)propionic acid was prepared again in the same conditions as given in Example 1.

As a result, the conversion of α-(4-isobutylphenyl)ethyl alcohol was 70.3% and the selectivity to α-(4-isobutylphenyl) propionic acid was 56.6%.

What is claimed is:

1. A process for recovering a catalyst comprising a nickel compound, a phosphine compound and an iodine compound used in the preparation of α-(4-isobutylphenyl)propionic acid by reacting α-(4-isobutylphenyl)ethyl alcohol with carbon monoxide to prepare a reaction product mixture comprising reaction products and catalyst components, which process comprises (a) recovering a part of the nickel compound as nickel carbonyl from a purge gas by collection of the nickel compound in a cold trap, (b) adding an organic solvent selected from the group consisting of hydrocarbons, ethers and esters to a concentrate of the reaction product mixture to extract the reaction products, wherein the extraction is carried out at 0° to 120° C. and (c) separating and recovering the majority of the catalyst components from the resultant extraction residue.

2. A process for recovering a catalyst according to claim 1, wherein the concentrate of the reaction product mixture is obtained by distillation under atmospheric pressure to 0.1 mmHg at 50° C. to 100° C.

3. A process for recovering a catalyst according to claim 1, wherein the organic solvent is selected from the group consisting of hexane, heptane, cyclohexane, benzene, toluene, diethyl ether, dioxane, tetrahydrofuran, methyl acetate and ethyl acetate.

4. A process for recovering a catalyst according to claim 3, wherein the organic solvent is selected from the group consisting of hexane and heptane.

5. A process for recovering a catalyst according to claim 1, wherein the extraction is carried out at 10° to 70° C.

6. The process according to claim 1, wherein the nickel compound is selected from the group consisting of nickel iodide, nickel acetate and nickel carbonyl complex.

7. The process according to claim 1, wherein the nickel compound is used in an amount of $10^{-3}$ to 1 gram of nickel atom per mole of α-(4-isobutylphenyl)ethyl alcohol.

8. The process according to claim 1, wherein the organic solvent is employed in an amount of less than 10 parts based on 1 part of the concentrate.

9. The process according to claim 1, wherein the organic solvent is employed in an amount of 1 to 5 parts based on 1 part of the concentrate.

10. The process according to claim 1, wherein the organic solvent is a hydrocarbon comprising n-hexane.

11. The process according to claim 1, wherein 10 to 25% of the nickel is recovered as said nickel carbonyl in (a).

12. The process according to claim 1, wherein 70 to 85% of the nickel is recovered in (c).

13. The process according to claim 1, wherein the catalyst comprises nickel recovered from (a) and (c).

14. The process according to claim 1, further comprising conducting a distillation to separate out the α-(4-isobutylphenyl) propionic acid and to recover a distillation residue.

15. A process according to claim 14, wherein the catalyst comprises nickel recovered from (a), (c) and the distillation residue.

16. The process according to claim 1, wherein the phosphine compound is selected from the group consisting of triphenylphosphine and tributylphosphine.

17. The process according to claim 1, wherein the iodine compound is selected from the group consisting of iodine and methyl iodide.

18. The process according to claim 1, wherein the concentrate of the reaction product mixture is obtained by distillation under atmospheric pressure to 0.1 mmHg at 50° C. to 100° C., the extraction is carried out at 0° to 120° C., and the solvent is employed in an amount of 1 to 5 parts based on 1 part of the concentrate.

19. The process according to claim 18, wherein the extraction is carried out at 10° to 70° C. and the solvent is n-hexane.

20. The process according to claim 18, wherein the nickel compound is selected from the group consisting of nickel iodide, nickel acetate and nickel carbonyl complex, said nickel compound being used in an amount of $10^{-3}$ to 1 gram of nickel atom per mole of α-(4-isobutylphenyl)ethyl alcohol, wherein the phosphine compound is selected from the group consisting of triphenylphosphine and tributylphosphine, wherein the iodine compound is selected from the group consisting of iodine and methyl iodide, wherein 10 to 25% of the nickel is recovered as said nickel carbonyl in (a), wherein 70 to 85% of the nickel is recovered in (c) and wherein the catalyst comprises nickel recovered from (a) and (c).

21. The process according to claim 20, wherein the extraction is carried out at 10° to 70° C. and the solvent is n-hexane.

22. The process according to claim 21, further comprising conducting a distillation to separate out the α-(4-isobutylphenyl)propionic acid and to recover a distillation residue.

* * * * *